United States Patent
Thacker et al.

(10) Patent No.: US 11,439,831 B2
(45) Date of Patent: *Sep. 13, 2022

(54) AUTOMATIC ADJUSTMENT TO MAINTAIN EVOKED POTENTIAL FEATURE

(71) Applicant: Boston Scientific Neuromodulation Corporation, Valencia, CA (US)

(72) Inventors: James R. Thacker, Eureka, MO (US); Harold Haut, Sea Cliff, NY (US); Robert Nathan, Hawthorne, NJ (US); David K. L. Peterson, Novato, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 380 days.

This patent is subject to a terminal disclaimer.

(21) Appl. No.: 16/588,014

(22) Filed: Sep. 30, 2019

(65) Prior Publication Data

US 2020/0023188 A1    Jan. 23, 2020

Related U.S. Application Data

(63) Continuation of application No. 15/933,194, filed on Mar. 22, 2018, now Pat. No. 10,456,585, which is a
(Continued)

(51) Int. Cl.
*A61N 1/372* (2006.01)
*A61N 1/36* (2006.01)

(52) U.S. Cl.
CPC ..... *A61N 1/37247* (2013.01); *A61N 1/36071* (2013.01); *A61N 1/36146* (2013.01); *A61N 1/36171* (2013.01); *A61N 1/36175* (2013.01)

(58) Field of Classification Search
CPC ............ A61N 1/36175; A61N 1/36146; A61N 1/37247
See application file for complete search history.

(56) References Cited

U.S. PATENT DOCUMENTS

| 3,646,940 A | 3/1972 | Timm et al. |
| 3,724,467 A | 4/1973 | Avery et al. |
(Continued)

FOREIGN PATENT DOCUMENTS

| EP | 2101870 B1 | 5/2017 |
| WO | WO-0143818 A1 | 6/2001 |
(Continued)

OTHER PUBLICATIONS

U.S. Appl. No. 11/553,447 U.S. Pat. No. 9,352,161, filed Oct. 26, 2006, Method of Maintaining Intensity Output While Adjusting Pulse Width or Amplitude.
(Continued)

*Primary Examiner* — William J Levicky
(74) *Attorney, Agent, or Firm* — Schwegman Lundberg & Woessner, P.A.

(57) ABSTRACT

Tissue stimulation systems generally include a pulse generating device for generating electrical stimulation pulses, at least one implanted electrode for delivering the electrical stimulation pulses generated by the pulse generating device, and a programmer capable of communicating with the pulse generating device. Stimulation pulses may be defined by several parameters, such as pulse width and amplitude. In methods of stimulating the tissue with the stimulation system, a user may adjust one of the parameters such as pulse width. The programmer may automatically adjust the pulse amplitude in response to the change in pulse width in order to maintain a substantially constant effect of the stimulation pulses.

20 Claims, 2 Drawing Sheets

Related U.S. Application Data continuation of application No. 15/152,336, filed on May 11, 2016, now Pat. No. 9,943,694, which is a continuation of application No. 11/553,447, filed on Oct. 26, 2006, now Pat. No. 9,352,161.

(56) References Cited

U.S. PATENT DOCUMENTS

| | | | |
|---|---|---|---|
| 3,822,708 | A | 7/1974 | Zilber |
| 4,340,063 | A | 7/1982 | Maurer |
| 4,343,301 | A | 8/1982 | Indech |
| 4,390,023 | A | 6/1983 | Rise |
| 4,923,437 | A | 5/1990 | Gordon |
| 4,977,895 | A | 12/1990 | Tannenbaum |
| 4,979,507 | A | 12/1990 | Heinz |
| 5,018,522 | A | 5/1991 | Mehra |
| 5,643,330 | A | 7/1997 | Holsheimer et al. |
| 5,766,230 | A | 6/1998 | Routh et al. |
| 5,913,882 | A | 6/1999 | King |
| 5,941,906 | A | 8/1999 | Barreras, Sr. et al. |
| 6,052,624 | A | 4/2000 | Mann |
| 6,266,558 | B1 * | 7/2001 | Gozani ............... A61B 5/1106 600/547 |
| 6,334,069 | B1 | 12/2001 | George et al. |
| 6,353,763 | B1 | 3/2002 | George et al. |
| 6,393,325 | B1 | 5/2002 | Mann et al. |
| 6,516,227 | B1 | 2/2003 | Meadows et al. |
| 6,587,724 | B2 | 7/2003 | Mann |
| 6,622,048 | B1 | 9/2003 | Mann et al. |
| 6,643,545 | B2 | 11/2003 | Ideker et al. |
| 6,662,051 | B1 | 12/2003 | Eraker et al. |
| 6,671,556 | B2 | 12/2003 | Osorio et al. |
| 6,928,320 | B2 | 8/2005 | King |
| 7,082,333 | B1 | 7/2006 | Bauhahn et al. |
| 7,123,961 | B1 | 10/2006 | Kroll et al. |
| 7,127,296 | B2 | 10/2006 | Bradley |
| 7,254,444 | B2 | 8/2007 | Moore et al. |
| 8,103,341 | B2 | 1/2012 | Libbus et al. |
| 9,352,161 | B2 | 5/2016 | Thacker et al. |
| 9,463,321 | B2 | 10/2016 | Bradley et al. |
| 9,943,694 | B2 | 4/2018 | Thacker et al. |
| 10,456,585 | B2 | 10/2019 | Thacker et al. |
| 2003/0074037 | A1 | 4/2003 | Moore et al. |
| 2003/0078623 | A1 | 4/2003 | Weinberg et al. |
| 2003/0093134 | A1 | 5/2003 | Bradley |
| 2003/0135245 | A1 | 7/2003 | Campos |
| 2003/0204224 | A1 | 10/2003 | Torgerson et al. |
| 2004/0034394 | A1 | 2/2004 | Woods et al. |
| 2004/0167586 | A1 * | 8/2004 | Overstreet ......... A61N 1/36039 607/48 |
| 2004/0210270 | A1 * | 10/2004 | Erickson ............ A61N 1/36071 607/46 |
| 2005/0107841 | A1 | 5/2005 | Meadows et al. |
| 2005/0245987 | A1 | 11/2005 | Woods et al. |
| 2005/0245993 | A1 | 11/2005 | Varrichio et al. |
| 2007/0265681 | A1 | 11/2007 | Gerber et al. |
| 2008/0103559 | A1 | 5/2008 | Thacker et al. |
| 2008/0114414 | A1 | 5/2008 | Moore et al. |
| 2016/0250489 | A1 | 9/2016 | Thacker et al. |
| 2018/0207432 | A1 | 7/2018 | Thacker et al. |

FOREIGN PATENT DOCUMENTS

| | | |
|---|---|---|
| WO | WO-2001043818 A1 | 6/2001 |
| WO | WO-2006110690 A1 | 10/2006 |

OTHER PUBLICATIONS

U.S. Appl. No. 15/152,336 U.S. Pat. No. 9,943,694, filed May 11, 2016, System and Method to Automatically Maintain Electrical Stimulation Intensity.

U.S. Appl. No. 15/933,194, filed Mar. 22, 2018, System and Method to Automatically Maintain Electrical Stimulation Intensity.

"U.S. Appl. No. 11/553,447 , Notice of Allowance dated Feb. 1, 2016", 5 pgs.

"U.S. Appl. No. 11/553,447, Advisory Action dated Feb. 28, 2012", 4 pgs.

"U.S. Appl. No. 11/553,447, Appeal Brief filed Jan. 7, 2013", 23 pgs.

"U.S. Appl. No. 11/553,447, Appeal Brief filed May 18, 2012", 12 pgs.

"U.S. Appl. No. 11/553,447, Appeal Decision mailed Jan. 4, 2016", 12 pgs.

"U.S. Appl. No. 11/553,447, Examiner Interview Summary dated Mar. 28, 2012", 3 pgs.

"U.S. Appl. No. 11/553,447, Examiner's Answer mailed Mar. 13, 2013", 8 pgs.

"U.S. Appl. No. 11/553,447, Final Office Action dated May 11, 2011", 9 pgs.

"U.S. Appl. No. 11/553,447, Final Office Action dated Jul. 22, 2010", 8 pgs.

"U.S. Appl. No. 11/553,447, Final Office Action dated Oct. 15, 2009", 8 pgs.

"U.S. Appl. No. 11/553,447, Final Office Action dated Dec. 20, 2011", 8 pgs.

"U.S. Appl. No. 11/553,447, Non Final Office Action dated Mar. 18, 2009", 9 pgs.

"U.S. Appl. No. 11/553,447, Non Final Office Action dated Aug. 7, 2012", 12 pgs.

"U.S. Appl. No. 11/553,447, Non Final Office Action dated Aug. 30, 2011", 11 pgs.

"U.S. Appl. No. 11/553,447, Non Final Office Action dated Dec. 22, 2010", 8 pgs.

"U.S. Appl. No. 11/553,447, Reply Brief filed May 13, 2013", 6 pgs.

"U.S. Appl. No. 11/553,447, Response filed Feb. 20, 2012 to Final Office Action dated Dec. 20, 2011", 5 pgs.

"U.S. Appl. No. 11/553,447, Response filed Mar. 16, 2011 to Non Final Office Action dated Dec. 22, 2010", 7 pgs.

"U.S. Appl. No. 11/553,447, Response filed Jun. 16, 2009 to Non Final Office Action dated Mar. 18, 2009", 8 pgs.

"U.S. Appl. No. 11/553,447, Response filed Jul. 26, 2011 to Final Office Action dated May 11, 2011", 10 pgs.

"U.S. Appl. No. 11/553,447, Response filed Oct. 2, 2010 to Final Office Action dated Jul. 22, 2010", 11 pgs.

"U.S. Appl. No. 11/553,447, Response filed Nov. 30, 2011 to Non Final Office Action dated Aug. 30, 2011", 11 pgs.

"U.S. Appl. No. 15/152,336, Advisory Action dated Sep. 13, 2017", 6 pgs.

"U.S. Appl. No. 15/152,336, Examiner Interview Summary dated Sep. 5, 2017", 1 pg.

"U.S. Appl. No. 15/152,336, Final Office Action dated Jul. 5, 2017", 24 pgs.

"U.S. Appl. No. 15/152,336, Non Final Office Action dated Mar. 3, 2017", 15 pgs.

"U.S. Appl. No. 15/152,336, Notice of Allowance dated Dec. 6, 2017", 7 pgs.

"U.S. Appl. No. 15/152,336, Preliminary Amendment filed May 12, 2016", 8 pgs.

"U.S. Appl. No. 15/152,336, Response filed Feb. 9, 2017 to Restriction Requirement dated Dec. 12, 2016", 8 pgs.

"U.S. Appl. No. 15/152,336, Response filed May 25, 2017 to Non Final Office Action dated Mar. 3, 2017", 10 pgs.

"U.S. Appl. No. 15/152,336, Response filed Aug. 30, 2017 to Final Office Action dated Jul. 5, 2017", 11 pgs.

"U.S. Appl. No. 15/152,336, Response filed Oct. 3, 2017 to Advisory Action dated Sep. 13, 2017", 15 pgs.

"U.S. Appl. No. 15/152,336, Restriction Requirement dated Dec. 12, 2016", 7 pgs.

"U.S. Appl. No. 15/933,194, Non Final Office Action dated Feb. 11, 2019", 12 pgs.

"U.S. Appl. No. 15/933,194, Notice of Allowance dated Jun. 19, 2019", 5 pgs.

"U.S. Appl. No. 15/933,194, Response filed May 13, 2019 to Non Final Office Action dated Feb. 11, 2019", 10 pgs.

"Australian Application Serial No. 2007308873, First Examiner Report dated Dec. 14, 2010", 3 pgs.

(56) References Cited

OTHER PUBLICATIONS

"Australian Application Serial No. 2007308873, Second Examiner Report dated Nov. 4, 2011", 3 pgs.
"Bioelectromagnetic Phenomena", The John Hopkins University, EN580.635, (Oct. 4, 2001), 11 pgs.
"Canadian Application Serial No. 2,667,623, Office Action dated Feb. 12, 2015", 5 pgs.
"European Application Serial No. 07844587.1, Examination Notification Art. 94(3) mailed Mar. 11, 2010", 4 pgs.
"European Application Serial No. 07844587.1, Examination Notification Art. 94(3) mailed Nov. 28, 2012", 4 pgs.
"European Application Serial No. 07844587.1, Response filed Mar. 25, 2013 to Examination Notification Art. 94(3) mailed Nov. 28, 2012", 7 pgs.
"European Application Serial No. 07844587.1, Response filed Jul. 20, 2010 to Examination Notification Art. 94(3) mailed Mar. 11, 2010", 7 pgs.
"International Application Serial No. PCT/US2007/082447, International Preliminary Report on Patentability dated Nov. 26, 2007", 8 pgs.
"International Application Serial No. PCT/US2007/082447, International Search Report dated Feb. 12, 2008", 4 pgs.
"International Application Serial No. PCT/US2007/082447, Written Opinion dated Feb. 12, 2008", 6 pgs.
"Reviewing the history of electrical stimulation and the devices crucial to its development", The First Stimulators, IEEE Engineering in Medicine and Biology, (1994), 532-542.
Reichel, M, et al., "Mobile PC-System for Intraoperative Electroneurodiagnostics", Department of Biomedical Engineering & Physics, University of Vienna, Department of Plastic and Reconstructive Surgery, University of Vienna, [Online]. Retrieved from the Internet: <http://www.ifess.org/cdrom_target/Vienna01/Posters/Reichei_Poster.htm>, (Jun. 16, 2005), 5 pgs.
Rise, Mark T, "Patterned Electrical Tissue Stimulator", [Online]. Retrieved from the Internet: <http://www.freepatentsonline.com/4390023.html>, (Jun. 16, 2005), 7 pgs.
Szeto, Andrew, "Relationship Between Pulse Rate and Pulse Width for a Constant-Intesity Level of Electrocutaneous Stimulation", Annals of Biomedical Engineering, vol. 13, (1985), 373-383.

\* cited by examiner

AUTOMATIC ADJUSTMENT TO MAINTAIN EVOKED POTENTIAL FEATURE

CLAIM OF PRIORITY

This application is a continuation of U.S. application Ser. No. 15/933,194, filed Mar. 22, 2018, which is a continuation of U.S. application Ser. No. 15/152,336, filed May 11, 2016, now issued as U.S. Pat. No. 9,943,694, which is a continuation of U.S. application Ser. No. 11/553,447, filed Oct. 26, 2006, now issued as U.S. Pat. No. 9,352,161, each of which is hereby incorporated by reference in its entirety.

BACKGROUND OF THE INVENTION

The present invention relates to tissue stimulation systems and more particularly to a clinically-adaptive stimulation programmer.

FIELD OF THE INVENTION

One example of a stimulation system is a spinal cord stimulation ("SCS") system. Spinal cord stimulation is a well-accepted clinical method for reducing pain in certain populations of patients. An SCS system typically includes an Implantable Pulse Generator (IPG) or a radio-frequency (RF) transmitter and receiver, electrodes, electrode leads, and when necessary, lead extensions. The electrodes are implanted along the dura of the spinal cord, and the IPG or RF transmitter generates electrical pulses that are delivered, through the electrodes, to the dorsal column and dorsal root fibers within the spinal cord. Individual electrode contacts (the "electrodes") are arranged in a desired pattern and spacing in order to create an electrode array. Individual wires within one or more electrode leads connect with each electrode in the array. The electrode leads exit the spinal column and attach to one or more electrode lead extensions, when necessary. The electrode leads or extensions are typically tunneled along the torso of the patient to a subcutaneous pocket where the IPG or RF-receiver is implanted.

Spinal cord stimulators and other stimulation systems are known in the art. For example, an implantable electronic stimulator is disclosed in U.S. Pat. No. 3,646,940 issued Mar. 7, 1972 for "Implantable Electronic Stimulator Electrode and Method" that provides timed sequenced electrical impulses to a plurality of electrodes. As another example, U.S. Pat. No. 3,724,467 issued Apr. 3, 1973 for "Electrode Implant for the Neuro-Stimulation of the Spinal Cord," teaches an electrode implant for the neuro-stimulation of the spinal cord. A relatively thin and flexible strip of physiologically inert plastic is provided as a carrier on which a plurality of electrodes are formed. The electrodes are connected by leads to an RF receiver, which is also implanted.

In U.S. Pat. No. 3,822,708, issued Jul. 9, 1974 for "Electrical Spinal Cord Stimulating Device and Method for Management of Pain," another type of electrical spinal cord stimulation device is taught. The device disclosed in the '708 patent has five aligned electrodes, which are positioned longitudinally on the spinal cord. Electrical pulses applied to the electrodes block perceived intractable pain, while allowing passage of other sensations. A patient operated switch allows the patient to adjust the stimulation parameters.

An SCS system treats chronic pain by providing electrical stimulation pulses through the electrodes of an electrode array located at the distal end of a lead placed epidurally next to a patient's spinal cord. The combination of electrodes used to deliver stimulation pulses to the targeted tissue constitutes an electrode configuration. In other words, an electrode configuration represents the polarity, being positive, negative, or zero, and for certain SCS systems with such capabilities, relative percentage of the current or voltage provided through each of the electrodes. Electrode arrays used with known SCS systems may employ between 1 and 16 electrodes on a lead. Electrodes are selectively programmed to act as anodes, cathodes, or left off, creating an electrode configuration. The number of electrodes available, combined with the ability to generate a variety of complex stimulation pulses, presents a huge selection of electrode configurations and stimulation parameters (together referred to herein as "stimulation sets") to the user.

Other parameters that may be controlled or varied in SCS include the frequency of pulses provided through the electrode array, pulse width, and the amplitude of pulses delivered. Amplitude may be measured in milliamps, volts, etc., as appropriate, depending on whether the system provides stimulation from current sources or voltage sources. With some SCS systems, the distribution of the current/voltage across the electrodes (including the case of the pulse generator or receiver, which may act as an electrode) may be varied such that the current is supplied via numerous different electrode configurations. In different configurations, different combinations of electrodes may provide current (or voltage) in different relative percentages of positive and negative current (or voltage). Moreover, there may be some electrodes that remain inactive for certain electrode configurations, meaning that no current is applied through the inactive electrode.

Programming processes are described in U.S. Pat. No. 6,622,048, herein incorporated by reference in its entirety. A stimulation programmer is utilized to instruct the pulse generating device to generate electrical stimulation pulses in accordance with selected parameters or stimulation sets. One known programmer for an IPG for SCS is called the BionicNavigator™, available from Advanced Bionics Corp., Sylmar, Calif. A stimulation programmer may be programmed by a technician attending the patient.

A stimulation programmer may be used in several scenarios. For example, when an SCS system is implanted, a procedure is performed to assure that the leads and/or electrodes are properly implanted in effective locations in the body. This programming usually takes place in an operating room. A navigation session is a procedure to select one or more effective stimulation sets for a particular patient. Such a session generally occurs after the leads and/or electrodes are implanted into a patient. Other programming sessions may include a "fitting" procedure, an extensive fitting procedure, a mapping procedure, a follow-up procedure, and an addition of a program procedure.

During the fitting of an SCS patient either in an operating room or after implantation, it is often desirable that the level of intensity of the stimulation be maintained, even though one or more parameters may be varied through the fitting session. Stimulus intensity is directly related to the pulse amplitude and pulse width and may be thought of as a perceived energy level delivered to the tissue to be stimulated. Such parameters that are varied during a fitting procedure include pulse width (PW) and amplitude (a). It is important to maintain a relatively constant electrical stimulus to the tissue in order to minimize patient discomfort during the fitting procedure.

Adjustments to the pulse width may result in changes in the recruitment of depolarized neural targets. However, changing the pulse width also affects the energy level delivered to the tissue. Therefore, during fitting it is desirable to change the recruitment but not the energy level delivered to the tissue. If an energy level or intensity of the stimulus is to be maintained while either amplitude or pulse width is changed, it is necessary to change both the pulse width and pulse amplitude.

For instance, a clinician adjusting the pulse width must be conscious of the effect of the intensity of the stimulus delivered to the tissue. Large changes in stimulation intensity can be uncomfortable for the patient, as can too high of a stimulation intensity. Likewise, too low of a stimulation level may not produce sufficient paresthesia to overcome the targeted pain. A clinician manually adjusting the pulse width therefore must also adjust pulse amplitude to maintain a constant energy level until the desired pulse width is achieved. Manually changing both the amplitude and the pulse width slows down the programming or fitting process. It is necessary to make small changes in pulse width and then make small changes in amplitude until the desired pulse width is achieved. Since the desired pulse width is often unknown until the patient verbally indicates the desired stimulation effect, adjustment is an iterative and sometimes painstaking process.

An automated system of adjusting the pulse width and/or amplitude while maintaining relatively constant stimulus intensity is thus desirable.

SUMMARY OF THE INVENTION

In accordance with one aspect of the present inventions, a method of operating a tissue stimulation system is provided. The method comprises placing at least one electrode in contact with the tissue of a patient. For example, the electrode(s) may be implanted within the patient in contact with the tissue. The method further comprises applying an electrical stimulus to the electrode(s), e.g., during a fitting procedure. The electrical stimulus comprises a plurality of pulses defined by a pulse width value and an amplitude value. The method further comprises adjusting (e.g., manually) one of the amplitude value and the pulse width value, and automatically adjusting the other of amplitude value and the pulse width value in response to the adjustment of the one of the amplitude value and the pulse width value, such that an effect of the electrical stimulus (e.g., a perceived stimulation intensity) remains substantially constant. That is, if the amplitude value is adjusted, then the pulse width value is automatically adjusted in response thereto, and if the pulse width value is adjusted, then the amplitude value is automatically adjusted in response thereto. Application of the electrical stimulus may be continuously applied to the tissue as the amplitude and pulse width values are adjusted, or discretely applied to the tissue, e.g., between adjustments in the amplitude and pulse width values.

In one method, the other of the amplitude value and the pulse width value is increased if the one of the amplitude value and the pulse width value is decreased, and the other of the amplitude value and the pulse width value is decreased if the one of the amplitude value and the pulse width value is increased. In another method, the other of the amplitude value and the pulse width value is automatically adjusted according to a relationship to maintain the electrical stimulus at a substantially constant intensity level. For example, the relationship $a/(1+k/PW)=a_x/(1+k/PW_x)$, wherein k is a constant of pulse frequency, wherein $a_x$ is the adjusted amplitude value, a is the amplitude value, $PW_x$ is the adjusted pulse width value, and PW is the pulse width value. In another method, the electrical stimulus is applied by a pulse generating device, and the adjustment of the other of the amplitude value and the pulse width value is automatically calculated by a programmer and communicated to the pulse generating device.

In accordance with a second aspect of the present inventions, a tissue stimulation system is provided. The tissue stimulation system comprises a pulse generating device for generating an electrical stimulus (defined in the same manner described above) to provide an effect in a patient (e.g., a perceived stimulation intensity), and at least one electrode for delivering the electrical stimulus generated by the pulse generating device. The pulse generating device may, e.g., be implantable. The tissue stimulation system further comprises an interface device capable of allowing a user to adjust (e.g., manually) one of the amplitude value and the pulse width value, and a programmer capable of programming the pulse generating device to control the generation of the electrical stimulus. The programmer is further capable of calculating an adjustment in the other of the amplitude value and the pulse width value in response to adjusting the one of the amplitude value and pulse width value, such that the effect of the electrical stimulus remains substantially constant. This can be accomplished in the same manner described above.

BRIEF DESCRIPTION OF THE DRAWINGS

The above and other aspects of the present invention will be more apparent from the following more particular description thereof, presented in conjunction with the following drawings wherein.

DETAILED DESCRIPTION OF THE EMBODIMENTS

It is to be understood that this invention is not limited to the particular devices, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to an "electrode" is a reference to one or more electrodes and equivalents thereof known to those skilled in the art, and so forth. Unless defined otherwise, all technical and scientific terms used herein have the same meanings as commonly understood by one of ordinary skill in the art. Although any methods, devices, and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

Although the methods of adjusting a stimulation parameter in response to an adjustment of another stimulation parameter will be described in reference to programming scenarios, the methods are equally application to stimulation sessions. A Spinal Cord Stimulation (SCS) system will be used herein as an example of a tissue stimulation system.

The various components of an exemplary SCS system may include an implantable pulse generator (IPG) and programmer used with such system. Implantable components may include an implantable pulse generator, one or more electrode arrays, and (as needed) one or more extensions to connect the array(s) to the IPG. Such implantable components, external devices and circuitry are more fully described in U.S. Pat. No. 6,622,048. Alternatively, a system comprised of an implanted RF receiver and external transmitter, as a pulse generating device in place of an IPG, may be used.

Figures 1, 2:
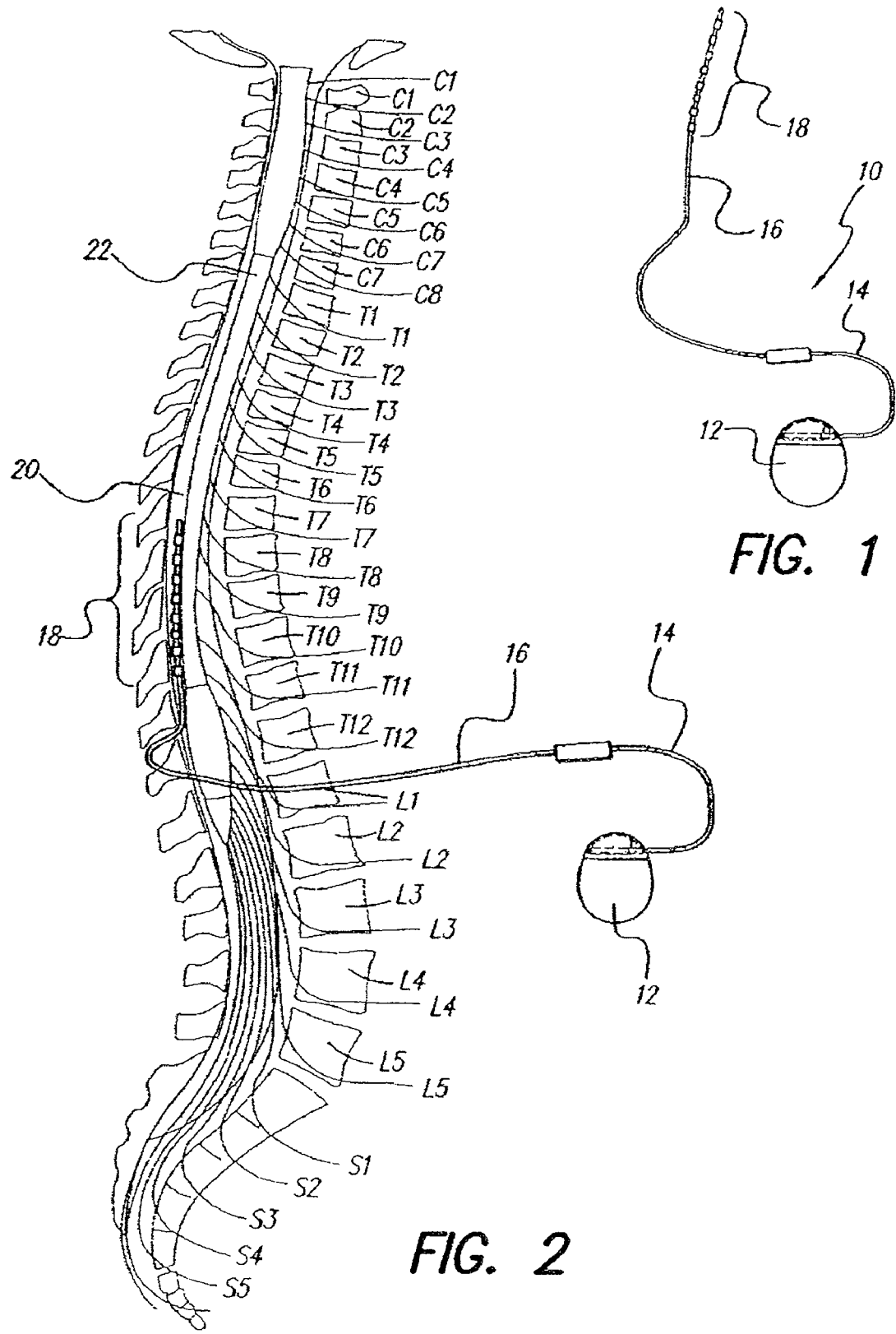
FIG. 1 depicts a Spinal Cord Stimulation (SCS) system, as an example of a tissue stimulation system.
FIG. 2 depicts the SCS system of FIG. 1 implanted in a spinal column.

An exemplary Spinal Cord Stimulation (SCS) system 10 is shown in FIG. 1. SCS system 10 comprises an Implantable Pulse Generator (IPG) 12, an optional lead extension 14, an electrode lead 16, and an electrode array 18. The IPG 12 generates stimulation current for implanted electrodes that make up the electrode array 18. When needed, a proximal end of the lead extension 14 is removably connected to the IPG 12 and a distal end of the lead extension 14 is removably connected to a proximal end of the electrode lead 16. Alternatively, a proximal end of lead 16 is attached directly to the IPG 12. Electrode array 18 is formed on a distal end of the electrode lead 16. The in-series combination of the lead extension 14 and electrode lead 16, carry the stimulation current from the IPG 12 to the electrode array 18.

The SCS system 10 described in FIG. 1 above is depicted implanted in the epidural space 20 in FIG. 2. The electrode array 18 is implanted at the site of nerve fibers that are the target of stimulation, e.g., along the spinal cord. Due to the lack of space near the location where the electrode lead 16 exits the spinal column, the IPG 12 is generally implanted in the abdomen or above the buttocks. When needed, the lead extension 14 facilitates locating the IPG 12 away from the electrode lead exit point. Another example of a SCS system that may be used with the present invention is described in U.S. Pat. No. 6,516,227, incorporated herein by reference in its entirety. Another stimulation system is described in U.S. Pat. No. 6,393,325 and related applications and issued patents. It is to be emphasized, however, that the invention herein described may be used with many different types of stimulation systems, and is not limited to use with the representative SCS system.

Electrical stimulation follows a well-known strength-duration relation. It is known that constant current rectangular pulses, such as biphasic pulses, may stimulate nerve and muscle, wherein the total stimulus charge Q at threshold increases linearly with the pulse duration d:

$$Q=k+bd,$$

wherein k and b are constants. The physicist Lapicque used capacitor discharge pulses to stimulate various tissues, and found that the threshold peak current, or intensity of the stimulation, I, varied inversely with the pulse duration of discharge, later to be known as pulse width (PW).

The relationship between intensity and pulse width was defined by Lapicque:

$$I=b^*(1+k/PW),$$

wherein I is intensity of an electrical stimulus, b represents the rheobase and k/PW stands for the ratio of chronaxie k to pulse width PW. Rheobase is an expression of the minimal strength (amplitude) of an electrical stimulus that is able to cause excitation of a tissue. Rheobase is generally expressed as a current value. Chronaxie is an expression of the minimum interval of time (pulse width) necessary to electrically stimulate a muscle or nerve fiber, using twice the minimum current needed to elicit a threshold response. Chronaxie, k, for the present purposes may be a constant of about 200 μs.

The intensity of neurostimulation is directly related to pulse amplitude (a). Using the relationship developed by Lapicque, known as the Lapicque Relationship, pulse amplitude (a) may be substituted for intensity. Therefore, the equation becomes:

$$a=b^*(1+k/PW).$$

As an example, suppose that 5 times the rheobase is an approximate level of intensity that is desirable during a stimulation session. Therefore, I=a=5b=b*(1+k/PW). To keep the intensity constant, a/(1+k/PW)=5. Therefore, for each amplitude value (a) and a constant intensity (I), a pulse width value may be determined.

If two different values of amplitude ($a_x$) and pulse width ($PW_x$) are plugged into the intensity-constant equation:

$$a/(1+k/PW)=a_x/(1+k/PW_x)=\text{a constant intensity}.$$

To determine the "new" value of amplitude ($a_x$), rearrange the equation to read:

$$a_x=a^*(1+k/PW_x)/(1+k/PW).$$

To determine the "new" value of pulse width ($PW_x$), rearrange the equation to read:

$$PW_x=k/[(a_x/a)^*(1+k/PW)-1].$$

To be consistent in notation, "PW" and "a" without subscripts will denote "original" or "previous" or "old" values of pulse width and amplitude, respectively. "$PW_x$" and "$a_x$" with subscript "x" will denote "next" or "new" values of pulse width and amplitude, respectively.

The populations of nerve fibers that are activated by the stimulus are diverse with respect to both effective chronaxie and rheobase. This diversity is in fact exploited by the present adjustment methods to achieve a more efficacious distribution of activated nerve fibers when pulse width and amplitude are increased and decreased relative to each other.

Therefore, if one changes the pulse width from PW to $PW_x$ and wants to adjust the amplitude (a to $a_x$) without changing the intensity, the new value of amplitude ($a_x$) would be:

$$a_x=a^*(1+k/PW_x)/(1+k/PW) \quad \text{(Equation No. 1)}.$$

Likewise, if one changes the amplitude (a to $a_x$) and wants to adjust the pulse width (PW to $PW_x$) without changing the intensity, the new value of pulse width ($PW_x$) would be:

$$PW_x=k/[(a_x/a)^*(1+k/PW)-1] \quad \text{(Equation No. 2)}.$$

Thus, after implanting at least one electrode in a patient for delivering electrical stimulation pulses generated by a pulse generating device, a pulse generator may apply an electrical stimulation pulse to the implanted electrode. The stimulation pulse may be defined by at least a pulse width value and an amplitude value. If a user through a programmer adjusts the value of the pulse width, then an automatic adjustment may be made to the amplitude without changing the level of stimulation intensity or the energy level delivered to the stimulated tissue. The energy output of the pulse generating device therefore would remain substantially constant, while a user adjusts the value of pulse width or amplitude and while the programmer automatically adjusts the other parameter.

In order to carry out the adjustment in values to the stimulation pulse, a stimulation programmer may interface with a user device and also with the implanted pulse generator. Programmers may be in the form of a conventional PC, a laptop, a tablet, a PDA, a monitor, a hand-held device, and any other suitable computing means. Alternatively, other logical means may used to make the adjustments to the amplitude and/or pulse width, such as a microprocessor within the pulse generator.

A user may make the adjustments to the amplitude or the pulse width through a suitable interface such as through a parameter screen. The screen may be displayed through any suitable interface device. Interface devices may include, but are not limited to, display screens, handheld devices, monitors, laptops, tablets and PDAs. The interface devices may be interactive, such as a touch screen. The user may use a mouse, joystick, or stylus in connection with the interface for the inputting her selections during programming. Thus, the selected user may input one or more parameter adjustments through the display screens. The programmer then recalculates the other stimulation parameters in order to maintain substantially constant stimulation intensity. The programmer communicates the adjustments to the pulse generating device. The electrical stimulation may be dynamically applied to the patient's tissue while the amplitude and pulse width values are adjusted, or can be applied to the patient's tissue between adjustments in the amplitude and pulse width values. Thus, the electrical stimulus may be characterized as being continuously applied to the patient's tissue or a discretely applied to the patient's tissue.

The users may be selected from the group consisting of patient, technician, clinician (such as a nurse, physician, physician's assistant, etc.), and combinations thereof. In one embodiment, the patient may be the selected user in order to allow maximum patient control. In another embodiment, the patient and attending clinician may share control of the programming session. In another embodiment, such as in an operating room, a clinician controls the programming alone.

The methods of the present invention may be incorporated into any tissue stimulation system, such as any SCS, neural or muscle stimulation system. Thus, in another embodiment, a tissue stimulation system is provided. A system may comprise: (1) a pulse generating device for generating electrical stimulation pulses; (2) at least one implanted electrode for delivering the electrical stimulation pulses generated by the pulse generating device; (3) a programmer, wherein the programmer is capable of instructing the pulse generating device to generate electrical stimulation pulses; and (4) an interface device for communicating with the programmer. The electrical stimulation pulses are defined by several parameters including a pulse amplitude and a pulse width. A user may communicate to the stimulation programmer through the interface device her adjustments of either the pulse width or the pulse amplitude. The programmer may thus calculate the appropriate change to be made to the pulse width or pulse amplitude, respectively, using the Equation Nos. 1 or 2.

In order to adjust the one or more stimulation parameters, a user may use a handheld device or other suitable interface that allows communication with the programmer. Any suitable user interface may be incorporated into embodiments of the invention. For example, the interfaces described in U.S. Pat. No. 6,393,325 may be used or altered for the programming sessions described herein.

Figure 3:
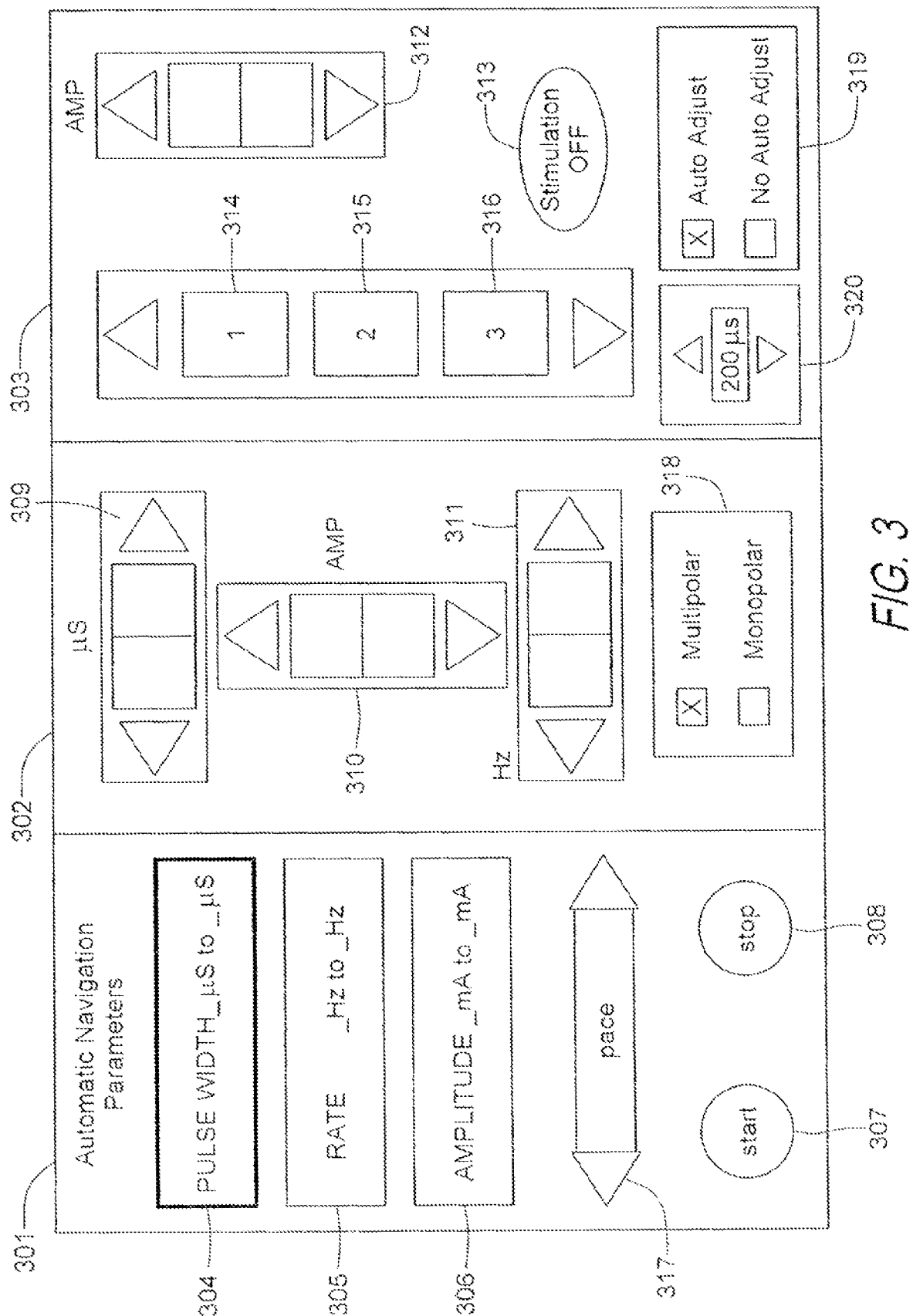
FIG. 3 depicts an exemplary user interface display.

An example of a programming screen may be the one illustrated in FIG. 3. As seen in FIG. 3, the interface may include three panels, or any combination or portion of the three panels (301, 302, 303). The user may be prompted to enter the parameters displayed in the 301 panel. These parameters may be set such as pulse width 304 and amplitude or strength 306. The user may also adjust the pace 317 of the programming session. Optionally, the parameters may include a rate 305. The interface may also have a start 307 and stop 308 button that halts or resumes the programming, respectively. In panel 301, a "begin" and an "end" value for a parameter are entered. In one embodiment, only a single parameter (e.g., pulse width 304) is highlighted to be auto-adjusted. Hitting the start 307 button begins the automatic adjustment of the highlighted stimulation parameter from its "begin" value through the minimum increment to its "end" value. This automated stepped adjustment can also take advantage of the auto adjust functionality between the PW and the pulse amplitude. With the interface in panel 302, the user may be able to manually adjust the pulse width 309, amplitude 310 or pulse rate or frequency 311, as well as select the between multipolar and monopolar stimulation 318, within the interface displayed at panel 302. In panel 303, a user may be able to adjust the amplitude 312. The user may entirely halt delivery of stimulation pulses, i.e., turn simulation off 313. The user may be able to select from 314, 315, and 316, which correspond to sets of electrode combinations to be tested.

One feature of the programming screen is an auto-adjust 319 enablement feature. If the auto-adjust feature 319 is selected, and if the user is changing the amplitude, the pulse width will be automatically adjusted by the programmer according to the Lapicque relationship as defined above. Likewise, if the user is changing pulse width, amplitude will be automatically adjusted by logical means according to the Lapicque relationship. By selecting the auto-adjust feature 319, the energy output is selected to be substantially constant though a user may be adjusting the amplitude or the pulse width. In the illustrated embodiment, the auto-adjust feature 319 is incorporated into a user interface as a check box on the programming screen. As another example, this auto-adjust feature 319 may be incorporated into the programming interface device as a button or key that is pressed when activated and then depressed when released, such as an Alt key. Other examples are easily incorporated into a parameter adjustment screen. Additionally, the user may find that the automatic adjustment results in an increasing or decreasing intensity of stimulation. This may be due to the incorrect assumption of the value of chronaxie of 200 us. Chronaxie has been shown to vary with the distance from the electrode to the stimulated nerves. Additionally, the fiber populations stimulated in SCS and other applications may have both a narrow range of chronaxies (as in pure dorsal column stimulation) or a wider range of chronaxies (as in root stimulation). So, the chronaxie value used for the automatic adjustment may be adjusted by the user using chronaxie adjustment feature 320 on the screen.

The calculation of pulse width and amplitude by Equation Nos. 1 and 2 for a given chronaxie k may maintain stimulus intensity during pulse width or amplitude adjustment. The automatic adjustment of the stimulation parameter achieved by the Equation Nos. 1 and 2 may be used in combination with a manual user adjustment of the other parameter. A user may, in some alternatives, select and release the auto-adjust feature to independently adjust the stimulation parameters manually. Once one of the parameters is selected by the user that is suitable, the user may activate the auto-adjust feature to lock-in the desirable parameter and work therefrom.

The present systems and methods of auto-adjusting one stimulation parameter according to an adjustment of another parameter are particularly useful in operating room programming. Patient comfort is particularly critical in the operating room. As explained above, it is desirable that the level of intensity of stimulation remain substantially constant even though the pulse width and amplitude may be changing. Programming for operating room programming may include the auto-adjust feature.

EXAMPLE

In Tables 1 and 2, a starting PW is 200 μs and a starting amplitude (a) is 4 mA. In Table 1, the pulse width is manually adjusted up to 1000 μs and then back down to 100 μs. The auto-adjust feature, using the Lapicque relationship, calculates the corresponding amplitude adjustments. In Table 1, the amplitude thus is auto-decreased to 2.4 mA and then increased to 6 mA. The constant, k, was set to 200 μs for the Example.

Table 2 illustrates how the pulse width would be auto-adjusted from manual changes to the amplitude (a). The amplitude in Table 2 is started at 4 mA, is increased to 6 mA and then decreased to 2.5 mA. The pulse width in Table 2, thus is auto-adjusted to decrease from 200 μs to 100 μs and then increase to 800 μs.

To avoid round-off problems, in one embodiment, a programmer may store a high precision working value of amplitude and pulse width known as "$a_{prog}$" and "$PW_{prog}$", respectively. As illustrated in Tables 1 and 2 below, the value of "$a_{prog}$" and "$PW_{prog}$" does not change through the iterations unless the amplitude is changed by the Lapicque Relationship equation by more than 0.1 mA or the pulse width is change by more than 10 μs. Thus, the programmed value of the amplitude and the pulse width is not changed to the calculated value of $a_x$ and $PW_x$, respectively, unless the adjustment calculated by the auto-adjust feature results in a change of more than 0.1 mA or 10 μs, respectively.

TABLE 1

Change pulse width ($PW_x$), auto-change amplitude ($a_x$)

| PW | a | $PW_x$ | $a_x$ | $a_{prog}$ |
|---|---|---|---|---|
| 200 | 4 | 220 | 3.818 | 3.8 |
| 220 | 3.818 | 240 | 3.667 | 3.7 |
| 240 | 3.667 | 260 | 3.538 | 3.5 |
| 260 | 3.538 | 280 | 3.428 | 3.4 |
| ... | ... | ... | ... | ... |
| 940 | 2.426 | 960 | 2.417 | 2.4 |
| 960 | 2.417 | 980 | 2.408 | 2.4 |
| 980 | 2.408 | 1000 | 2.4 | 2.4 |
| 1000 | 2.4 | 980 | 2.408 | 2.4 |
| 980 | 2.408 | 960 | 2.417 | 2.4 |
| 960 | 2.417 | 940 | 2.426 | 2.4 |
| 940 | 2.426 | 920 | 4.5 | 2.4 |
| ... | ... | ... | ... | ... |
| 160 | 4.5 | 140 | 4.857 | 4.9 |
| 140 | 4.857 | 120 | 5.333 | 5.3 |
| 120 | 5.333 | 100 | 6 | 6 |
| 100 | 6 | 80 | 7 | 7 |

TABLE 2

Change amplitude ($a_x$), auto-change pulse width ($PW_x$)

| a | PW | $a_x$ | $PW_x$ | $PW_{prog}$ |
|---|---|---|---|---|
| 4 | 200 | 4.1 | 190.5 | 190 |
| 4.1 | 190.5 | 4.2 | 181.8 | 180 |
| 4.2 | 181.8 | 4.3 | 173.9 | 170 |
| 4.3 | 173.9 | 4.4 | 166.7 | 170 |
| ... | ... | ... | ... | ... |
| 5.7 | 108.1 | 5.8 | 105.3 | 110 |
| 5.8 | 105.3 | 5.9 | 102.6 | 100 |
| 5.9 | 102.6 | 6 | 100 | 100 |
| 6 | 100 | 5.9 | 102.6 | 100 |
| 5.9 | 102.6 | 5.8 | 105.3 | 110 |
| 5.8 | 105.3 | 5.7 | 108.1 | 110 |
| 5.7 | 108.1 | 5.6 | 111.1 | 110 |
| ... | ... | ... | ... | ... |
| 2.8 | 500 | 2.7 | 571.4 | 570 |
| 2.7 | 571.4 | 2.6 | 666.7 | 670 |
| 2.6 | 666.7 | 2.5 | 800 | 800 |
| 2.5 | 800 | 2.4 | 1000 | 1000 |

It has been demonstrated that maintaining the level of stimulation intensity delivered to the stimulation tissue substantially maintains the stimulation intensity perceived by the patient at a constant level, e.g., so that the patient always experiences comfortable paresthesia while the parameter values are adjusted (i.e., as one of the amplitude value and pulse width value is manually adjusted by the user while the other of the amplitude vale and pulse width value is automatically adjusted. While maintaining the level of stimulation intensity constant in accordance with Equation Nos. 1 and 2 has been found to be suitable in maintaining the perceived stimulation intensity of the patient at a constant, there may be other functions that can be used. For example, a charge applied to the tissue may be maintained at a constant level, or the energy of the stimulation applied to the tissue may be approximated using other equations, e.g., pulse width multiplied by the square of the current.

While the amplitude and pulse width values of the stimulus have been previously described as being adjusted to maintain an actual stimulation intensity applied to the tissue, and thus, perceived level of stimulation, the amplitude and pulse width values may be adjusted to maintain other stimulation effects. For example, other stimulation effects that may be automatically maintained at a substantially constant level include, but are not limited to, gross area and/or distribution of paresthesia, features of evoked potentials (e.g., EP amplitude, conduction velocity, etc.), estimates of tissue blood flow and/or perfusion, changes in muscle tone and/or tremor, features of EEG, features of EMG, and metrics of cardiac function (e.g., heart rate, ST segment level, etc.).

In addition, while it been found that the automated adjustment of the amplitude value in view of a manual adjustment in the pulse width value, or vice versa, provides an efficient and effective means for maintaining a stimulation effect, it is possible to automatically adjust other parameters values of the electrical stimulus (e.g., the frequency rate of the pulses) in response to the manual adjustment of either or both of the amplitude value and pulse width value, or vice versa.

For example, the total energy of the electrical stimulus linearly varies in accordance with the frequency rate of the pulses. In this case, as either or both of the amplitude value and pulse width value are manually increased or decreased, the frequency rate of the pulses may automatically be decreased or increased to maintain the stimulation effect. Or, as the frequency rate of the pulses is manually increased or decreased, either or both of the amplitude value and pulse width value can be automatically decreased or increased to maintain stimulation effect.

As another example, increasing the length of the rise-time and fall-time of a stimulus pulse is somewhat equivalent to decreasing pulse width, and vice versa. That is, if the stimulus effect is a result of the total charge transfer (area under the current-time curve) per phase, changing the shape of the pulse to maintain charge transfer constant in response to a change in amplitude or pulse width is equivalent to changing only the pulse width or amplitude. In this case, as the amplitude value and/or pulse width value is manually increased or decreased, the rise-time and/or fall-time of the stimulus pulses may automatically be increased or decreased to maintain the stimulation effect. Or, as the rise-time and/or fall-time of the stimulus pulses is manually increased or decreased, the amplitude value and/or pulse width value may automatically be increased or decreased to maintain the stimulation effect.

While the invention herein disclosed has been described by means of specific embodiments and applications thereof, numerous modifications and variations could be made thereto by those skilled in the art without departing from the scope of the invention set forth in the claims. For example, the methods discussed above are not limited to spinal cord stimulation systems and may be used with many kinds of stimulation systems such as, but not limited to, those described above, cochlear implants, cardiac stimulation systems, peripheral nerve stimulation systems, muscle tissue stimulation systems, brain stimulation systems and microstimulators.

What is claimed is:

1. A system, comprising:
a programmer configured to instruct a stimulator to deliver electrical current defined by adjustable stimulation parameters to at least one electrode to provide at least one evoked potential feature, wherein the adjustable stimulation parameters have a defined relationship to the at least one evoked potential feature and include at least a first stimulation parameter and a second stimulation parameter,
wherein the programmer is configured to automatically respond to an adjustment of at least the first stimulation parameter, and then maintain the at least one evoked potential feature at a substantially constant level by automatically adjusting at least the second stimulation parameter, using the defined relationship, in response to adjusting the at least the first stimulation parameter.

2. The system of claim 1, wherein:
the at least one evoked potential feature includes at least one of an evoked potential amplitude or an evoked potential conduction velocity; and
the defined relationship includes a defined relationship of one or more of a pulse amplitude, a pulse width, a pulse frequency or a pulse frequency to the at least one evoked potential feature.

3. The system of claim 1, wherein the adjustable stimulation parameters at least partially define a pulse shape, and the defined relationship includes a defined relationship of the pulse shape to the at least one evoked potential feature.

4. A method, comprising:
delivering electrical current defined by adjustable stimulation parameters to at least one electrode to provide at least one evoked potential feature, wherein the adjustable stimulation parameters have a defined relationship to the at least one evoked potential feature and include at least a first stimulation parameter and a second stimulation parameter; and
adjusting at least the first stimulation parameter, and then maintaining the at least one evoked potential feature at a substantially constant level by automatically adjusting at least the second stimulation parameter, using the defined relationship, in response to adjusting the at least the first stimulation parameter.

5. The method of claim 4, wherein the at least one evoked potential feature includes an evoked potential amplitude.

6. The method of claim 4, wherein the at least one evoked potential feature includes an evoked potential conduction velocity.

7. The method of claim 4, wherein:
the defined relationship includes a defined relationship of a pulse rise time, a pulse fall time, and a pulse amplitude to the at least one evoked potential feature,
the first stimulation parameter includes the pulse amplitude, and
the at least the second parameter includes at least one of the pulse rise time or the pulse fall time.

8. The method of claim 4, wherein:
the defined relationship includes a defined relationship of a pulse rise time, a pulse fall time, and a pulse width to the at least one evoked potential feature,
the first stimulation parameter includes the pulse width, and
the at least the second parameter includes at least one of the pulse rise time or the pulse fall time.

9. The method of claim 4, wherein:
the defined relationship includes a defined relationship of a pulse rise time, a pulse fall time, and a pulse width to the at least one evoked potential feature,
the first stimulation parameter includes the pulse width, and
the first stimulation parameter includes a pulse frequency, and the at least the second parameter includes at least one of a pulse rise time or a pulse fall time.

10. The method of claim 4, wherein the defined relationship includes a defined relationship of a pulse amplitude, a pulse width and a pulse frequency to the at least one evoked potential feature.

11. The method of claim 10, wherein the first stimulation parameter includes the pulse amplitude, and the at least the second parameter includes at least one of the pulse width or the pulse frequency.

12. The method of claim 10, wherein the first stimulation parameter includes the pulse width, and the at least the second parameter includes at least one of the pulse amplitude or the pulse frequency.

13. The method of claim 10, wherein the first stimulation parameter includes the pulse frequency, and the at least the second parameter includes at least one of the pulse amplitude or the pulse width.

14. The method of claim 4, wherein the adjustable stimulation parameters at least partially define a pulse shape, and the defined relationship includes a defined relationship of a pulse shape to the at least one evoked potential feature.

15. The method of claim 4, wherein:
the at least one evoked potential feature includes at least one of an evoked potential amplitude or an evoked potential conduction velocity; and
the defined relationship includes a defined relationship of one or more of a pulse amplitude, a pulse width, a pulse frequency or a pulse frequency to the at least one evoked potential feature.

16. A non-transitory machine-readable medium including instructions, which when executed by a machine, cause the machine to:
deliver electrical current defined by adjustable stimulation parameters to at least one electrode to provide at least one evoked potential feature, wherein the adjustable stimulation parameters have a defined relationship to the at least one evoked potential feature and include at least a first stimulation parameter and a second stimulation parameter; and adjust at least the first stimulation parameter, and then maintain the at least one evoked potential feature at a substantially constant level by automatically adjusting at least the second stimulation parameter, using the defined relationship, in response to adjusting the at least the first stimulation parameter.

17. The non-transitory machine-readable medium of claim 16, wherein:

the at least one evoked potential feature includes at least one of an evoked potential amplitude or an evoked potential conduction velocity; and the defined relationship includes a defined relationship of one or more of a pulse amplitude, a pulse width, a pulse frequency or a pulse frequency to the at least one evoked potential feature.

18. The non-transitory machine-readable medium of claim 16, wherein the first stimulation parameter includes the pulse amplitude, and the at least the second parameter includes at least one of the pulse width or the pulse frequency.

19. The non-transitory machine-readable medium of claim 16, wherein the first stimulation parameter includes the pulse width, and the at least the second parameter includes at least one of the pulse amplitude or the pulse frequency.

20. The non-transitory machine-readable medium of claim 16, wherein the first stimulation parameter includes the pulse frequency, and the at least the second parameter includes at least one of the pulse amplitude or the pulse width.

* * * * *